(12) United States Patent
Wang

(10) Patent No.: US 8,521,442 B2
(45) Date of Patent: Aug. 27, 2013

(54) METHOD AND DEVICE FOR MEASURING THE ELECTRICAL CONDUCTIVITY AND/OR RESISTIVITY OF A SOLUTION

(75) Inventor: Changlin Wang, Shanghai (CN)

(73) Assignee: Mettler-Toledo AG, Greifense (CH)

( * ) Notice: Subject to any disclaimer, the term of this patent is extended or adjusted under 35 U.S.C. 154(b) by 914 days.

(21) Appl. No.: 12/333,595

(22) Filed: Dec. 12, 2008

(65) Prior Publication Data
US 2009/0125250 A1    May 14, 2009

Related U.S. Application Data

(63) Continuation of application No. PCT/EP2007/058946, filed on Aug. 28, 2007.

(30) Foreign Application Priority Data

Aug. 30, 2006 (CN) .......................... 2006 1 0030555

(51) Int. Cl.
*G06F 19/00* (2011.01)
(52) U.S. Cl.
USPC .............. 702/30; 324/439; 324/442; 324/444
(58) Field of Classification Search
USPC ............................. 702/30; 324/439/442/444
See application file for complete search history.

(56) References Cited

U.S. PATENT DOCUMENTS

| | | | |
|---|---|---|---|
| 4,683,435 A | 7/1987 | Blades | |
| 4,808,930 A | 2/1989 | Kaiser | |
| 5,260,663 A * | 11/1993 | Blades | 324/442 |
| 5,708,363 A * | 1/1998 | Yates et al. | 324/442 |
| 6,369,579 B1 | 4/2002 | Riegel | |

FOREIGN PATENT DOCUMENTS

| | | |
|---|---|---|
| CN | 1459629 A | 12/2003 |
| CN | 1619318 A | 5/2005 |
| DE | 35 17 772 A1 | 11/1986 |
| DE | 42 33 110 A1 | 4/1994 |
| DE | 198 15 922 A1 | 10/1999 |
| EP | 0 911 639 A1 | 4/1999 |
| JP | H3-210466 | 9/1991 |
| JP | 2004-219326 | 8/2004 |
| WO | WO 88/01740 A1 | 3/1988 |

* cited by examiner

OTHER PUBLICATIONS

International Search Report (PCT/ISA/210), Nov. 26, 2007.

*Primary Examiner* — Jonathan C Teixeira Moffat
*Assistant Examiner* — Hien Vo
(74) *Attorney, Agent, or Firm* — Buchanan Ingersoll & Rooney PC

(57) ABSTRACT

An exemplary method for measuring the electrical resistance and/or electrical conductivity of solutions, includes: exciting the electrodes with a rectangular shaped, alternating current of a certain frequency $f_H$ through a connecting cable; synchronously rectifying a voltage of the electrodes of the measuring cell in response to the alternating current, calculating a first average voltage, dividing the first average voltage by the current amplitude to obtain a first impedance $R_H$; then exciting the electrodes with a rectangular shaped, alternating current of another frequency $f_L$ through the connecting cable; synchronously rectifying the voltage of the electrodes in response to the alternating current, calculating a second average voltage, and dividing the second average voltage by the current amplitude to obtain a second impedance $R_L$. Based on a mathematical model, a relation between the resistance R between the electrodes to be measured and the first and second impedances $R_H$ and $R_L$, and the ratio n of the frequency $f_H$ to $f_L$ is established, so as to derive the resistance R between the electrodes. The conductivity of the solution can be derived by incorporating an electrode constant.

32 Claims, 3 Drawing Sheets

METHOD AND DEVICE FOR MEASURING THE ELECTRICAL CONDUCTIVITY AND/OR RESISTIVITY OF A SOLUTION

RELATED APPLICATIONS

This application claims priority under 35 U.S.C. §119 to Chinese Application 200610030555.6 filed in China on Aug. 30, 2006, and as a continuation application under 35 U.S.C. §120 to PCT/EP2007/058946 filed as an International Application on Aug. 28, 2007 designating the U.S., the entire contents of which are hereby incorporated by reference in their entireties.

TECHNICAL FIELD

A method is disclosed for measuring the electrical conductivity or resistivity of solutions and in particular to a method, which is capable of eliminating the negative influences of electrode polarization and long connecting cables on the measurements.

BACKGROUND INFORMATION

A common procedure for measuring the electrical conductivity comprises placing two electrodes in a solution, supplying electricity to the solution through the electrodes, measuring the voltage U across the ends of the electrodes and measuring the current I flowing there between. The resistivity of the solution is determined by calculating the resistance R between the two electrodes according to the expression $R = U \cdot I^{-1}$. Further, the conductivity G of the solution is given by the expression $G = C \cdot R^{-1}$, where C is the electrode constant and R is the resistance between the electrodes. The conductivity is the reciprocal of the resistivity of the solution.

However, uniformly directed current between the electrodes in the solution will also decompose (i.e., polarize) the solution and thereby produce an electromotive counter force. The counter force, known as the effect of polarization, decreases the current flow or involves higher exiting voltages and consequently introduces a dynamically changing measurement error. Consequently the measured resistance of the solution will drift with time. A common way to address the measurement error caused by this polarization is to use an alternating current for the measurement.

For an ideally short connecting cable arranged between the electrodes and the measurement circuit the measurement accuracy will rise with an increasing current frequency. However, this does not hold for practical connecting cables since there always exists a certain cable capacitance, which leads to an increased error at higher frequencies. Therefore, reducing the cable length and increasing the frequency of the current are two ways to increase the accuracy of the measurements, but these parameters can also interfere with each other.

CN1619318 A discloses a method, in which the electrodes are excited by sine signals of two different frequencies. As a result, a modulus $|Z_a|$ and $|Z_b|$ for each of the two impedances $Z_a$ and $Z_b$ is obtained, as well as the ratio $r = |Z_a| \cdot |Z_a|^{-1}$. The electrical conductivity G of the solution can then be calculated according to the expression:

$$G = K^{-1} \cdot \left( |Z_a| \cdot \sqrt{1 + \frac{r^2 - 1}{4 - r^2}} \right)$$

with K being the cell constant and r being the ratio of the two impedances $Z_a$ and $Z_b$. The disclosed method addresses only the effect of polarization: But this method does not address (e.g., eliminate) the effect of the electrode polarization as well as the effect of a long cable simultaneously.

CN1459629 discloses a method for performing a measurement based on a concept of usable power. By measuring the voltage and the current of a solution, the expression:

$$G = C \cdot \frac{\int I^2 dt}{\int U \cdot I dt}$$

is applied to obtain the electrical conductivity G of the solution. This method addresses the effect of polarization but again, this method does not address (e.g., eliminate) both effects.

DE 4 233 110 A1 discloses a method for determining an exciting frequency. A base frequency and an adjacent frequency, which differs about 20% from the base frequency, is used to conduct two measurements. If the difference between the results of these measurements is small, the used base frequency is considered to be right; otherwise the base frequency will be changed and new measurements will be conducted. This can be repeated until optimal frequencies are found, and the error can be estimated. Nevertheless, this method is a known single frequency method.

U.S. Pat. No. 6,369,579 B1 discloses a method to reduce the error in a determination of the conductivity of a solution with a measurement converter and an alternating voltage at two frequency values. The method and the equivalent circuit diagram consider the effects within the measurement cell, but not the cable capacitance. The disclosed solution is not suitable in cases with long connecting cables.

In general, for an actual measurement setup, both the capacitance of the cable and the polarization of the electrode exist simultaneously, regardless of the used frequency, Therefore, the known methods do not address (e.g., eliminate) errors arising from both effects simultaneously.

SUMMARY

A method for measuring the electrical resistance (R) and/or electrical conductivity (G) of a solution with a measurement device having at least one measuring cell, which is in contact with the solution and which is connected via a connecting cable to a processing unit, the method comprising: applying an alternating current (i) to the measuring cell; measuring, using the processing unit, a voltage (V) of the measuring cell in response to an alternating current; and determining, from the voltage (V) of the measuring cell, the electrical resistance (R) and/or the electrical conductivity (G) of the solution, wherein the alternating current (i), which is provided by a current source and which is applied to the at least one measuring cell is of substantially rectangular shape, wherein a capacitive effect of the connecting cable is included in an equation, and wherein the electrical resistance (R) and/or the electrical conductivity (G) of the solution is determined by solving the equation using a calculation unit.

A device is disclosed for measuring the electrical resistance (R) and/or electrical conductivity (G) of a solution, comprising: at least one measuring cell, configured to contact a solution and connected via a connecting cable to a processing unit, which is suitable for measuring a voltage (V) of the measuring cell and for determining from the voltage (V) of the measuring cell a resistance (R) and/or a conductivity (G) of the solution; a current source configured to provide an alternating current (i) of substantially rectangular shape; and a calculation unit configured for calculating the resistance (R) and/or the conductivity (G) of the solution from the voltage (V) of the measuring cell in response to the alternating current by solving an equation which accounts for a capacitive effect of the connecting cable.

BRIEF DESCRIPTION OF THE DRAWINGS

Features and advantages of the present disclosure will now be described with reference to the accompanying drawings and the specific embodiments thereof. The Figures show.

DETAILED DESCRIPTION

Figure 1:
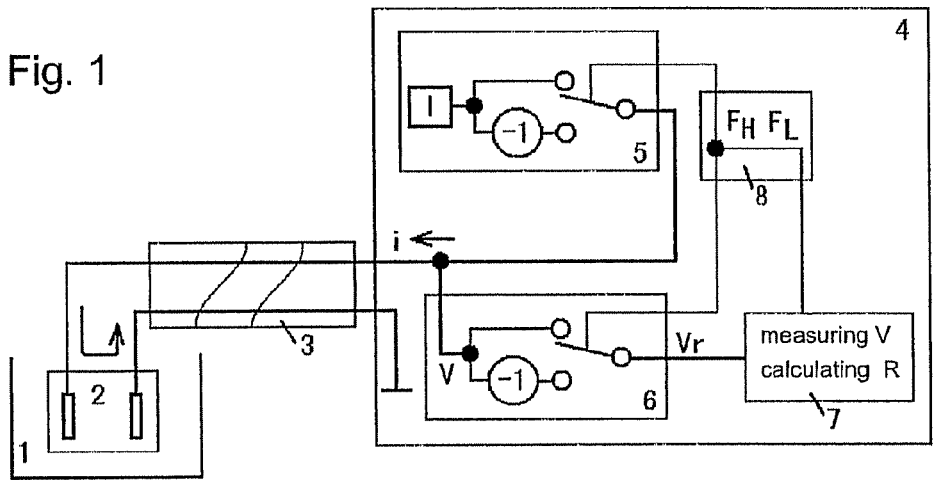
FIG. 1 a schematic diagram illustrating an exemplary method for measuring solution conductivity according to a first embodiment for 2-pole electrodes of a 2-wire system.

Exemplary embodiments are directed to measurement of conductivity or electrical resistance of solutions.

For example, rectangular shaped, alternating current can be used to provide a precise result with a relatively low frequency. The low frequency in turn can allow a simple and cost effective design of the measurement device. Further, processing of a voltage of the measurement cell in response to the alternating current (e.g., electrical current related to the alternating current at least in part) can be relatively simple and can be accomplished by performing elementary calculations.

The calculations can be performed by a calculation unit which is arranged within a processing unit. However, the calculation unit can also be arranged separately in another device, such as a transmitter or a computer or a terminal. The term measurement device is used herein in a broad, comprehensive sense.

Components of the processing unit, such as an input of an amplifier or a synchronous rectifier, can be configured to operate in a range well below saturation. However, the frequency of the alternating current can be chosen to be high enough to avoid effects due to polarization of the solution at the electrodes of the measurement device. By properly choosing the frequency of the alternating current, the method according to the disclosure can eliminate the adverse influence of the electrode polarization as well as that of the cable capacitance.

The disclosed method can be very advantageous, as even for long connecting cables between the electrodes and the processing unit and an existing electrode polarization, very accurate measurement results can be obtained for solution conductivity by using a relatively simple circuit and relatively simple procedures.

In a further embodiment of the disclosure, the measuring cell includes at least two electrodes with one electrode connected to a common potential, such as a ground potential. These electrodes can be arranged in a single electrode configuration or in a 4-pole electrode configuration and/or in a 2-pole electrode configuration, which can comprise a 2-wire connection or a 4 wire connection.

In an exemplary embodiment of the disclosure, the capacitive effect of the connecting cable and/or of the polarization effect of the solution is accounted for (e.g., included in) an equation, and the resistance and/or conductivity of the solution is determined by solving that equation.

In a further exemplary embodiment of the disclosure, the processing unit controls generation of the alternating current and/or synchronization of the alternating current in relation to a rectification process, and/or synchronization of a rectification process in relation to the alternating current.

Further, a first measurement with an alternating current of a first frequency and a second measurement with an alternating current of a second frequency can be performed. The two frequencies can be different, and the ratio between the higher frequency ($f_H$) and the lower frequency ($f_L$): $n=f_H/f_L$ is, for example, between 1.20 and 4. This can have an advantage that even though a measurement error is always present regardless of the frequency used for the measurement, an accurate result can be calculated based on the measurement results obtained with the two different frequencies. This method could be called a dual-frequency method.

In an exemplary configuration, the current source includes a constant current source and an alternating device to reverse the direction of the constant current.

In another embodiment of the disclosure, the voltage of the measuring cell is processed by a rectification process, which can be synchronised to the alternating current, and by an averaging process, for example by averaging with a low pass filter, to provide an averaged voltage. From these, an impedance of the solution can be calculated by dividing the averaged voltage by the amplitude of the corresponding alternating current. Further, the resistance of the solution can be calculated from the first impedance of the first measurement and the second impedance of the second measurement.

The rectification process can be performed by a processing unit, which includes a synchronous rectifier that is connected to the calculation unit. Thus, the at least one measuring cell is connected, if appropriate via an amplifier, to the input of the synchronous rectifier. In addition, the calculation unit can include a low pass filter, which filters and/or averages the input signal of the calculation unit.

In a further embodiment, the resistance of the solution is calculated according to the expression: $R=P_{nw}R_L+(1-P_{nw})R_H$, wherein $P_{nw}$ is a function of the ratio (n) and of the relative difference (w), which is defined as $w=(R_L-R_H)R_H^{-1}$.

In a further embodiment, a reference value ($w_{ref}$) is defined and in the case that the relative difference (w) is close to or smaller than the reference value ($w_{ref}$), the function $P_{nw}$ is given by: $P_{nw}=n/(n-1)$.

In another embodiment of the disclosure, the voltage of the measuring cell is measured using at least three different points in time to determine at least three voltages values, and the resistance is calculated by simultaneously solving at least three equations, which are given by a time dependent function of the voltage of the measuring cell for each of the at least three voltages values. This can, for example, be accomplished by an analog-digital converter suitable to convert the measured electrode voltage (i.e., measurement cell responding voltage), at high speed, in particular during a fraction of the time period of a half cycle of the alternating current. The voltage values can also be determined by measuring the voltage of the measuring cell during a time period and by averaging the measurements over the corresponding time period.

In an exemplary configuration of the measurement device, the calculation unit includes an analog-digital converter suitable to convert the electrode voltage of the measuring cell, for example at high speed, in particular during a fraction of the time period of a half cycle of the alternating current. For example, the calculation unit can be configured to calculate the resistance by simultaneously solving at least three equations for three unknowns R, B and D, with R being the value to be measured, which are given by a time dependent function of the voltage of the measuring cell for each of at least three voltages values $V_1$, $V_2$ and $V_3$.

Figure 2:
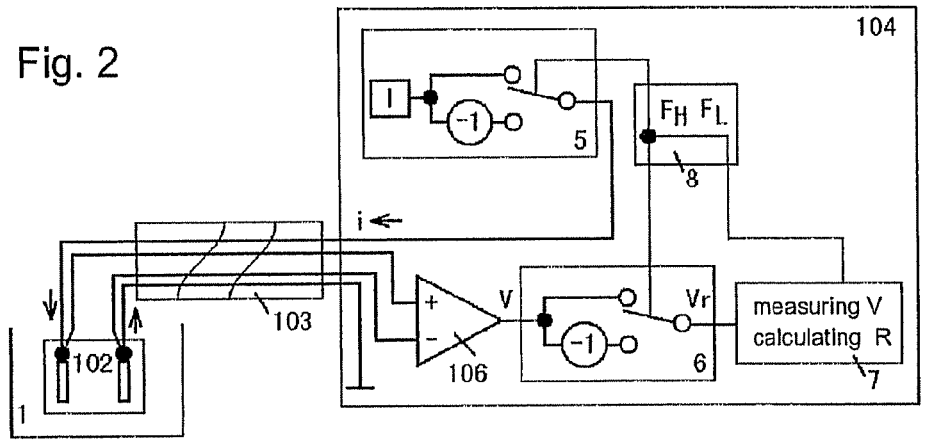
FIG. 2 a schematic diagram illustrating an exemplary method for measuring solution conductivity according to a first embodiment for 2-pole electrodes of a 4-wire system.
Figure 3:
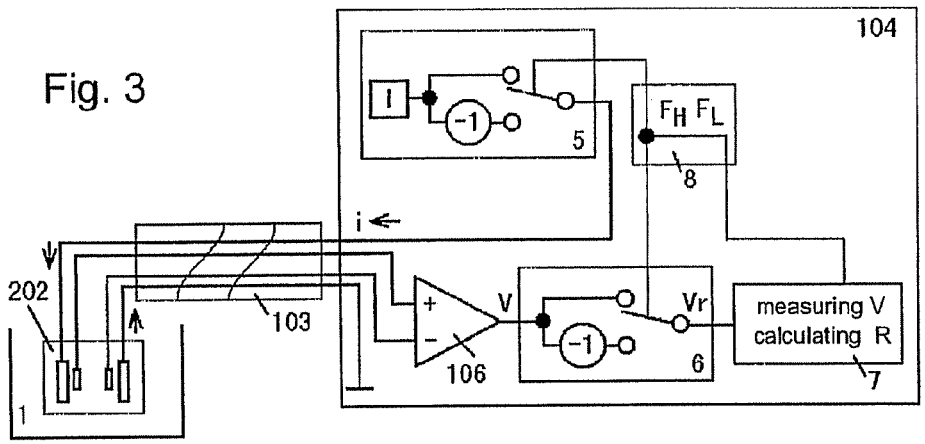
FIG. 3 a schematic diagram illustrating an exemplary method for measuring solution conductivity according to a first embodiment for 4-pole electrodes of a 4-wire system.

In a further embodiment, the time dependent function of the voltage of the measuring cell can be given by the expression:

$$V = R \cdot I_H \cdot \left[ B^2 \left(1 - \frac{2}{1+D} \cdot D^{t/T_H}\right) + B \cdot (1-B) \cdot \ln(D) \cdot \left(0.5 - \frac{t}{T_H}\right) \right]$$

wherein $B = \frac{C_p}{C_s + C_p}$, $D = e^{-\frac{T_H}{T}}$ and $T = \frac{C_s C_p}{C_s + C_p} R$ with $C_p$ representing the capacitance of the polarization effect which is generated in the solution (1) of FIGS. 1 to 3 by the measuring cell (2, 102, 202); $C_s$ representing the sum of the capacitance of the cable (3, 103) and/or the capacitance of the processing unit (4, 104) and/or the distribution capacitance of the measuring cell (2, 102, 202); $T_H$ representing the time period of a half cycle of the period T of alternating current (i) having an amplitude $I_H$. For example, the following intermediate values are calculated:

$$B_1 = \frac{V_1 + V_3}{V_2}, \quad B_2 = \frac{V_1}{V_2}$$

or, as will be described below, in an exemplary embodiment wherein averaged voltages are used for three different periods of time:

$$B_1 = \frac{V_{a1} + V_{a3}}{V_{a2}}, \quad B_2 = \frac{V_{a1}}{V_{a2}},$$

$$D = \left(\frac{B_1 - 1 - \sqrt{2B_1 - 3}}{2 - B_1}\right)^4,$$

$$P_1 = \left(1 - \frac{2}{1+D} D^{1/4}\right),$$

$$P_2 = \left(1 - \frac{2}{1+D} D^{1/2}\right),$$

-continued $$B = \left(1 - 4 \cdot \frac{P_1 - B_2 \cdot P_2}{\ln(D)}\right)^{-1},$$

and resistance (R) of the solution (1) is calculated according to the expression:

$$R = \frac{V_2}{I_H \cdot B^2 * P_2} \text{ or, if applicable } R = \frac{V_{a2}}{I_H \cdot B^2 \cdot P_2}.$$

The solving of the time dependent function of the voltage of the measuring cell can be accomplished by a calculation unit that is suitable to calculate the resistance by simultaneously solving the at least three equations. In particular, the three measured voltage values can then be used to set up three simultaneous equations for solving the three unknown values R, B and D, with R being the value to be measured. This method can be named as the triple-voltage method, as three voltage values are used for the calculations.

FIGS. 1 to 3 are schematic diagrams illustrating a principle of a solution conductivity measurement method according to a first exemplary embodiment of the present disclosure. Referring now to FIG. 1, the measurement system comprises a 2-pole electrode 2 inserted in the solution 1 to be measured, a processing unit 4 and a connecting cable 3. The processing unit 4 includes a current source 5, which produces a rectangular shaped, alternating current, a synchronous rectifier 6, an operation unit 7 and a dual-frequency controlling unit 8. The electrodes in FIG. 1 use 2-pole electrodes of 2-wire connection, and the current source 5 outputs the rectangular shaped, alternating current to one of the electrodes via the connecting cable. The synchronous rectifier 6 receives a electrode voltage from the connecting cable, wherein the voltage is a responding voltage which is in response to the alternating current.

It is to be noted, that a 2-pole electrode of a 4-wire connection as shown in FIG. 2 may also be used. In that case, the electrode 102 is connected to the processing unit 104 via the 4-wire connecting cable 103 and the synchronous rectifier 6 acquires a voltage V of the measuring cell between the two electrodes via the amplifier 106. The current flowing in two wires connected to the amplifier 106 can be neglected, as the input impedance of the amplifier 106 is very high. Furthermore, the influence of the conductive wire resistance of the long connecting cable 103 can be neglected, as the rectangular shaped, alternating current excitation is equivalent to constant current excitation.

Alternatively, the 4-pole electrode 202 of the 4-wire connection as shown in FIG. 3 can also be utilized, wherein a 4-pole electrode 202 is connected to the processing unit 104. This kind of 4-wire connection can eliminate not only the influence of the conductor resistance of the long connecting cable 103, but can also reduce the effect of electrode polarization to some extent.

For the different types of connections described above, the same measurement method can be used namely, the dual-frequency method or the triple-voltage method as described hereinafter.

Figure 4:
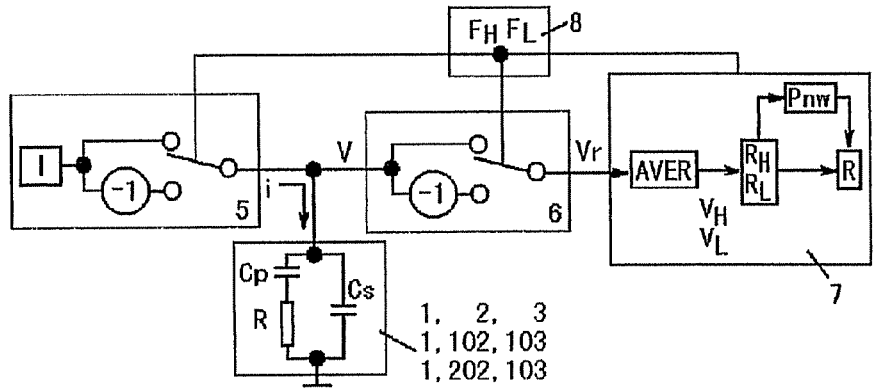
FIG. 4 a schematic diagram showing a principle diagram of an exemplary solution conductivity measurement method of the first embodiment of the present disclosure.
Figure 5:
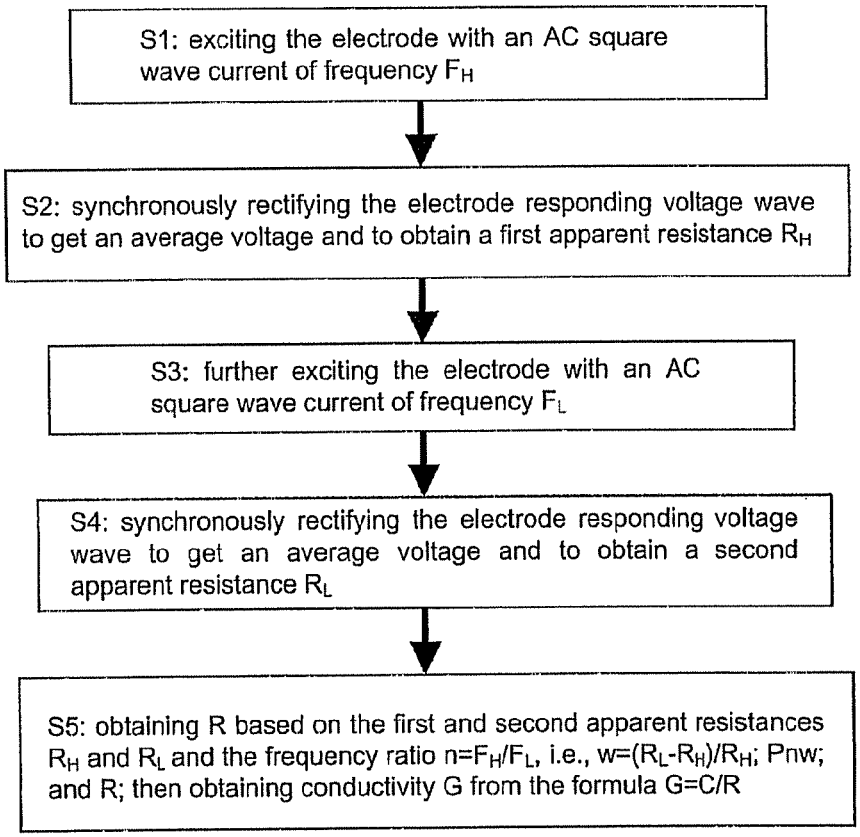
FIG. 5 a schematic flow chart representing steps of an exemplary solution conductivity measurement method according to a first embodiment of the present disclosure.

The so-called dual-frequency method is disclosed in FIGS. 4 to 5 and described in the following paragraphs:

FIG. 4 is an equivalent diagram of a solution conductivity measurement method according to the first exemplary embodiment of the present disclosure. In FIG. 4, $R = C \cdot G^{-1}$ is the resistance between the electrodes to be measured, with G being the conductivity of the solution and C the electrode constant. The capacitor $C_p$ represents the equivalent capacitance caused by electrode polarization, while capacitor $C_s$ represents the sum of the equivalent capacitance of the cable, the capacitance of the input circuit of the meter and the distribution capacitance of the electrode. Current I is of constant amplitude, namely, $I_H$ or $I_L$; frequency $F_H$ and $F_L$ represent two exciting frequencies. Voltage V represents the responding electrode voltage. $V_r$ represents the voltage function after the synchronous rectification procedure.

As a first embodiment the dual-frequency method and their basic principle will now be briefly described.

A measurement is carried out under excitation by a rectangular shaped, alternating current of a certain frequency. The error caused by the capacitance of the long cable is mainly introduced during the transition of a direction change of the current. This error is directly proportional to the ratio between the transition duration and the half cycle period of the excitation. The transition duration is almost the same between two measurements, even when the exciting frequency is different, but the half cycle period differs between two measurements. Therefore the error is smaller with lower frequency compared to a higher frequency.

Assuming that the transition duration is $t_1$. The half cycle period of the frequency $F_H$ is $$T_H = \frac{1}{2F_H}$$

and $R_H$ is the impedance measured with a rectangular shaped, alternating exciting current of frequency $F_H$. Similar, the half cycle period of the frequency $F_L$ is $$T_L = \frac{1}{2F_L}$$

and $R_L$ is the impedance measured with a rectangular shaped, alternating exciting current of frequency $F_L$.

Let $$\frac{T_L}{T_H} = \frac{F_H}{F_L} = n$$

be the ratio of the frequency.
Then $$R_H = R \cdot \left(\frac{T_H - t_1}{T_H}\right) \text{ and } R_L = R \cdot \left(\frac{T_L - t_1}{T_L}\right)$$

and then $$R = \left(\frac{n}{n-1}\right) \cdot R_L + \left(\frac{-1}{n-1}\right) \cdot R_H = \left(\frac{n}{n-1}\right) \cdot R_L + \left(1 - \frac{n}{n-1}\right) \cdot R_H$$

In particular, if n=2, then: $R = 2R_L - R_H$

Figure 6:
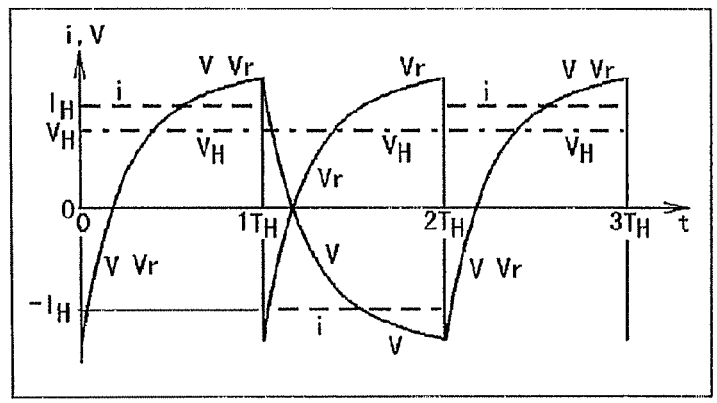
FIG. 6 a schematic diagram showing exemplary current and voltage functions.

The method described above is a simplified description of the method, but it helps to understand the essence of the dual-frequency measurement method. How to accurately determine the resistance R between the electrode will now be described in detail with reference to the exemplary equivalent circuit model shown in FIG. 4, the flow chart of the measurement steps according to the first embodiment of the disclosure shown in FIG. 5 and the schematic diagram of current and voltage functions shown in FIG. 6.

The method includes:

In a first step S1 the electrode 2 (102,202) is excited with a rectangular shaped, alternating current via cable 3 (103). By analyzing the equivalent circuit shown in FIG. 4 a function of the voltage V of the measuring cell can be derived as described below:

During the short measurement period the resistance R between the electrodes, and the capacitances $C_s$ and $C_p$ are assumed to be constant. It is assumed, that the electrodes are excited with a rectangular shaped, alternating current of amplitude $I_H$ and a frequency $F_H$. During the positive half period of the current (from t=0 to $T_H$) i equals $I_H$ and under the capacitance current law:

$$C_s \frac{dV}{dt} = i_{C_s} \text{ and } C_p \frac{dV_p}{dt} = i_{C_p}$$

Further in accordance with the Kirchhoff's current law:

$$C_s \frac{dV}{dt} = i - C_p \frac{dV_p}{dt}$$

If Kirchhoff's voltage law is applied to both ends of the capacitor $C_p$, then:

$$V_p = V - \left(i - C_s \frac{dV}{dt}\right) \cdot R.$$

Let $$B = \frac{C_P}{C_s + C_P},$$

$$T = \frac{C_s C_P}{C_s + C_P} R \text{ and}$$

$$A = \frac{I_H}{C_s + C_P} = \frac{I_H \cdot R * B \cdot (1 - B)}{T},$$

then the following differential equation is obtained:

$$T \frac{d^2 V}{dt^2} + \frac{dV}{dt} = A.$$

The general solution of the differential equation is:

$$V = C_1 e^{-\frac{1}{T}} + At + C_2.$$

Assuming that the electrodes and the excitation are at steady state, then:

$$V(t=T_H) = -V(t=0)$$

$$V_p(t=T_H) = -V_p(t=0)$$

Let $$D = e^{-\frac{T_H}{T}}, \text{ then}$$

$$C_1 = -\frac{2 \cdot I_H \cdot R}{1+D} \cdot B^2 \text{ and}$$

$$C_2 = I_H R \left[ B^2 - \frac{1}{2}B(1-B)\frac{T_H}{T} \right]$$

then the function of the voltage V of the measuring cell is:

$$V = R * I_H \cdot \left[ B^2 \cdot \left(1 - \frac{2}{1+D} D^{t/T_H}\right) + B \cdot (1-B) \cdot \ln(D) \cdot \left(\frac{1}{2} - \frac{t}{T_H}\right) \right]$$

In step S2 the synchronous rectification is applied to the voltage V of the measuring cell to determine a first average voltage. Then dividing it by the current amplitude, the first impedance $R_H$ will be obtained. The mathematical expression will be described in more detail below.

First, averaging the electrode voltage during a time period $T_1 \rightarrow T_2$:

$$V_a = \frac{1}{T_2 - T_1} \int_{T_1}^{T_2} V dt$$

gives:

$$V_a = R \cdot I_H \left\{ B^2 \left[1 - \frac{2}{(1+D)} \cdot \frac{T}{(T_2-T_1)} \cdot \left(D^{\frac{T_1}{T_H}} - D^{\frac{T_2}{T_H}}\right)\right] + B \cdot (1-B) \cdot \ln(D) \cdot \left[\frac{1}{2} - \frac{1}{2}\frac{(T_2+T_1)}{T_H}\right] \right\}$$

If a complete half period is averaged ($T_1=0$, $T_2=T_H$), then the first average of voltage is:

$$V_H = R \cdot I_H \cdot B^2 \left[1 - \frac{1-D}{1+D} \cdot \frac{2T}{T_H}\right] = R \cdot I_H \cdot B^2 \cdot [1 - E(D)]$$

with $E(D) = \frac{2 \cdot (1-D)}{(1+D)[-\ln(D)]}$.

By applying synchronous rectification, the average voltage of the second half period ($T_H \rightarrow 2T_H$) will be as same as that of the first half period ($0 \rightarrow T_H$), that is, the same as the total average of the voltage function after the synchronous rectification. The first impedance is defined as:

$$R_H = \frac{V_H}{I_H} = R * B^2 [1 - E(D)].$$

In step S3 the rectangular shaped, alternating current of another frequency is used to excite the electrode 2 through the connecting cable 3. Assuming the exciting current is a rectangular shaped, alternating current with an amplitude of $I_L$ and a frequency $f_L$, if the relation between $f_L$ and the first rectangular shaped, alternating current is $f_H/f_L=n$ and $T_L/T_H=n$, then the function of the voltage V of the measuring cell can also be derived as:

$$V = R * I_L \cdot \left[ B^2 \cdot \left(1 - \frac{2}{1+D^n} \cdot (D^n)^{t/T_H}\right) + B \cdot (1-B) \cdot \ln(D^n) \cdot \left(\frac{1}{2} - \frac{t}{n*T_H}\right) \right]$$

In step S4 the synchronous rectification is applied to the voltage V of the measuring cell to determine a second average voltage and a second impedance $R_L$ when dividing it by the current amplitude.

The average voltage after the synchronous rectification can be expressed as:

$$V_L = RI_L \cdot B^2 \left[1 - \frac{1-D^n}{1+D^n}\frac{2T}{n \cdot T_H}\right] = RI_L \cdot B^2 [1 - E(D^n)]$$

And the second impedance is defined as:

$$R_L = \frac{V_L}{I_L} = R \cdot B^2 [1 - E(D^n)]$$

In step S5 the resistance R between the electrodes can be calculated based on the first and the second impedances $R_H$, $R_L$ and the ratio n of the frequencies $F_H$ and $F_L$. The conductivity of the solution to be measured can be obtained by further incorporation of the electrode constant. The specific calculation can be expressed as follows:

Let the relative difference of the two impedances be $$w = \frac{R_L - R_H}{R_H},$$

then $$w = \frac{E(D) - E(D^n)}{1 - E(D)}$$

Further, it follows that $$R = P_{nw} R_L + (1 - P_{nw}) R_H$$

with $$P_{nw} = P_n(w) = \frac{E(D) + [1/B^2 - 1]}{E(D) - E(D^n)} \approx \frac{E(D)}{E(D) - E(D^n)}$$

The expression $P_{nw}$ can be sufficiently accurate assuming that $$\frac{1}{B^2} - 1 = 0.$$

In that case $P_{nw}$ is a function of n and w. First, n is defined and then the function $P_n(w)$ can be obtained in advance by using the numerical method with a segmented polynomial fitting. The specific method can be described as follows: A series of D values is listed, then a series of w and $P_n(w)$ values are derived based on the respective D values. These values are used for the segmented polynomial fitting. During the measurement, the relative difference $w=(R_L-R_H)/R_H$ of the two impedances $R_H$, $R_L$ is calculated first, then $P_{nw}$ is calculated and the resistance R between the electrodes can be obtained thereafter. By using the expression G=C/R, the solution conductivity G can be calculated, wherein C is the electrode constant.

The present method, theoretically, will work as long as the ratio n of two frequencies is not equal to 1. In reality, however, in order to reduce the effects of other random interferences, the frequency ratio can be, for example, between 1.2 to 4, or the reciprocal thereof, that is, between 0.25 and 0.84.

Two examples of the frequency ratio n are provided below.
Example 1, if n=2:
When w>0.53:

$$P_{nw} = \frac{0.038599 \cdot w^4 - 0.309326 \cdot w^3 + 0.950803 \cdot w^2 - 1.422355 \cdot w + 5.761831}{3 - w}$$

When 0.11<w≦0.53:

$$P_{nw} = -1.566025 \cdot w^4 + 1.885248 \cdot w^3 - 0.042810 \cdot w^2 - 0.059616 \cdot w + 2.004903$$

When w≦0.11:

$$P_{nw} = 2$$

In particular, when n=2 and $$w = \frac{R_L - R_H}{R_H} < 0.11$$

then $R = 2R_L - R_H$.

Example 2, if n=3/2=1.5:
When w>0.23:

$$P_{nw} = \frac{2.472277 \cdot w^4 - 6.618677 \cdot w^3 + 7.091540 \cdot w^2 - 3.932823 \cdot w + 3.766115}{(1.25 - w)}$$

When 0.067<w≦0.23:

$$P_{nw} = -65.905750 w^4 + 46.746107 w^3 - 6.836475 w^2 + 0.370457 w + 2.993219$$

When w≦0.067:

$$P_{nw} = 3$$

In particular, when n=1.5 and $$w = \frac{R_L - R_H}{R_H} < 0.067$$

then $R = 3R_L - 2R_H$.

The expression above may be simplified according to the actual accuracy requirement. The theoretical relative error caused by an inaccurate calculation of $P_{nw}$ can be analyzed in the following way:
assume $P_{nw}$ becomes $P_{nw1}$, the relative difference is:

$$Err = \frac{[P_{nw1} \cdot R_L + (1 - P_{nw1}) \cdot R_H)] - [P_{nw} \cdot R_L + (1 - P_{nw}) \cdot R_H]}{[P_{nw} \cdot R_L + (1 - P_{nw}) \cdot R_H]}$$

-continued $$= \frac{(P_{nw1} - P_{nw}) \cdot w}{1 + w \cdot P_{nw}}$$

By numerical value analysis, it can be determined that for Example 1 where n=2 the expression above will give a theoretical relative error of Err<0.01% caused by inaccurate calculation of $P_{nw}$ when w<0.53 w.; For Example 2 where n=1.5, the expression above will give a theoretical relative error of Err<0.01% caused by inaccurate calculation of $P_{nw}$ when w<0.76.

When the relative difference w is smaller than a reference value $w_{ref}$, $$P_{nw} = \frac{n}{n - 1}$$

can be used.

According to the numerical value analysis, when n=1.2 to 4, the following estimation can be used:
if w<$-0.0209 \cdot n^2 + 0.194 \cdot n - 0.151$ (first reference value), or w<0.15|n=2, or w<0.09|n=1.5, the theoretical relative error caused by inaccurate calculation of $P_{nw}=n/(n-1)$ will then be Err<0.02%;
if w<$-0.0238 \cdot n^2 + 0.247 \cdot n - 0.197$ (second reference value), or w<0.20|n=2, or w<0.12|n=1.5, the theoretical relative error caused by inaccurate calculation of $P_{nw}=n/(n-1)$ will then be Err<0.1%.

The reference value $w_{ref}$ can be selected according to the calculation accuracy requirement: A smaller reference value $w_{ref}$ leads to a smaller relative error according to the formula $P_{nw}=n/(n-1)$.

During the measurement it can be assumed, that $I_H=I_L=I$, therefore some expressions can even be further simplified.

In the present embodiment, the synchronous rectifier 6 can be implemented as hardware circuit, such as a multiplex switch. As the expression only uses the average voltage for the dual-frequency method, a low pass filter can be inserted to follow the synchronous rectifier and to precede the A/D converter. This can reduce the speed requirement for the A/D converter. Alternatively, the synchronous rectifier 6 can also be implemented in a software after a high speed A/D conversion of the voltage V of the measuring cell.

A further embodiment of the present disclosure discloses a method, which can be named triple-voltage method and which is described in the following paragraphs.

If the speed of the A/D converter is high enough, it is also possible to excite only with a rectangular shaped, alternating current of a single frequency. The adverse effects of the electrode polarization and the long connecting cable on the measurement accuracy of the electrical conductivity can also be addressed (e.g., eliminated) using the following method for the measurement.

Figure 7:
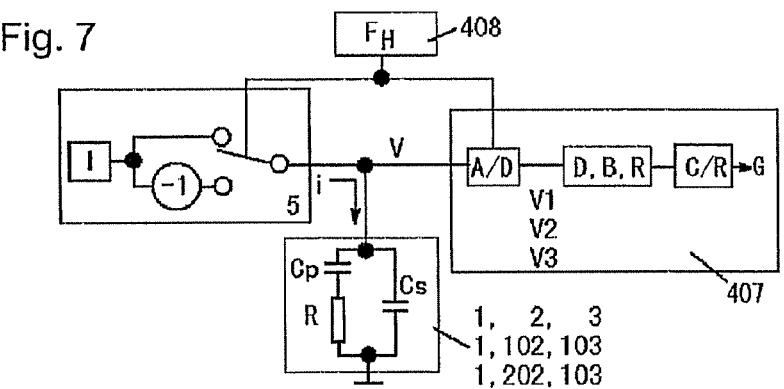
FIG. 7 a schematic diagram illustrating a principle of an exemplary solution conductivity measurement method according to a second embodiment of the present disclosure.

FIG. 7 is a schematic diagram showing the principle of the measurement method for the solution conductivity determination according to a further exemplary embodiment of the present disclosure. The method works with a measurement circuit similar to FIG. 4 but the synchronous rectifier 6 can be omitted and the voltage signal can be sent directly to the operation unit 407.

Figure 8:
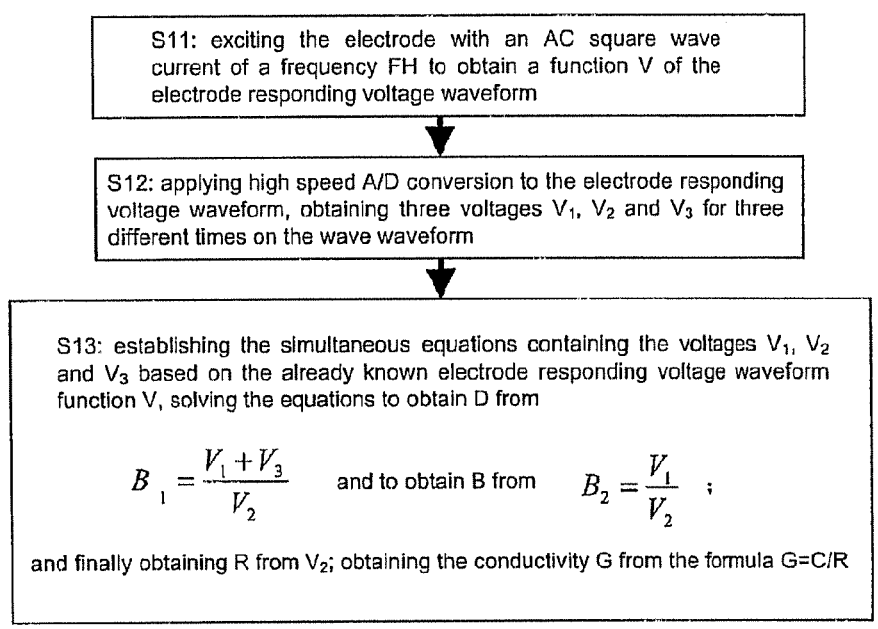
FIG. 8 a flow chart representing steps of an exemplary solution conductivity measurement method according to a second embodiment of the present disclosure.

FIG. 8 is a schematic flow chart showing the steps of an exemplary measurement method for the solution conductivity determination according to this embodiment. The test system includes a current source 5, which provides a rectangular shaped, alternating exciting current, a frequency controlling unit 408 and an operation unit 407.

Referring to FIGS. 7 and 8, the method of the present embodiment includes the steps of:

Step S11: Exciting the electrodes with a rectangular shaped, alternating current of a certain amplitude and a certain frequency through the cable. Assuming an excitation with a rectangular shaped, alternating current having the amplitude $I_H$, and the frequency $f_H$, for the positive half cycle, as described above, the function of the function of the function of the voltage V of the measuring cell is:

$$V = R \cdot I_H \left[ B^2 \left(1 - \frac{2}{1+D} D^{t/T_H}\right) + B(1-B)\ln(D)\left(\frac{1}{2} - \frac{t}{T_H}\right) \right]$$

The voltage function has three independent variables D, B, R, which can be derived by using three voltages at different times or by using three average voltages for different time periods.

Step S12: Applying a high speed A/D conversion to the voltage V of the measuring cell and obtaining three voltages for different times or three average voltages for three periods during half the period of the alternating current. For example, the voltage is A/D converted to get three voltages $V_1$, $V_2$ and $V_3$ for three points of time ($t_1$, $t_2$, $t_3$), namely, $t_1=\frac{1}{4}T_H$, $t_2=\frac{1}{2}T_H$, and $t_3=\frac{3}{4}T_H$, of the voltage function V.

Step S13: Establishing the simultaneous equations for $V_1$, $V_2$ and $V_3$ according to the already known function of the voltage V of the measuring cell $$V = R \cdot I_H \left[ B^2 \left(1 - \frac{2}{1+D} D^{t/T_H}\right) + B(1-B)\ln(D)\left(\frac{1}{2} - \frac{t}{T_H}\right) \right] \text{ as:}$$

$$V_1 = V(t_1) = R \cdot I_H \left[ B^2 \left(1 - \frac{2}{1+D} D^{1/4}\right) + B(1-B)\ln(D)\left(\frac{1}{4}\right) \right]$$

$$V_2 = V(t_2) = R \cdot I_H \left[ B^2 \left(1 - \frac{2}{1+D} D^{1/2}\right) \right]$$

$$V_3 = V(t_3) = R \cdot I_H \left[ B^2 \left(1 - \frac{2}{1+D} D^{3/4}\right) + B(1-B)\ln(D)\left(-\frac{1}{4}\right) \right]$$

wherein R is the resistance between the electrodes to be measured.

Again, let $$B = \frac{C_P}{C_s + C_P}, D = e^{-\frac{T_H}{T}} \text{ and } T = \frac{C_s C_P}{C_s + C_P} R$$

with $T_H$ being the half period of the frequency $F_H$. The three independent parameters R, B and D can be derived by solving the simultaneous equations. The solution conductivity G can then be derived from the formula G=C/R.

One way to solve the equations is described below:

$$B_1 = (V_1 + V_3) \cdot (V_2)^{-1}$$

$$= \left(1 - \frac{2}{1+D} D^{1/4}\right) \cdot \left(1 - \frac{2}{1+D} D^{3/4}\right) \cdot \left(1 - \frac{2}{1+D} D^{1/2}\right)^{-1}$$

D can be derived from $B_1$:

$$D = \left(\frac{B_1 - 1 - \sqrt{2B_1 - 3}}{2 - B_1}\right)^4, \text{ then}$$

$$B_2 = \frac{V_1}{V_2} = \left[\left(1 - \frac{2}{1+D} D^{1/4}\right) + (B^{-1} - 1) \cdot \left(\frac{1}{4}\ln(D)\right)\right] \cdot \left(1 - \frac{2}{1+D} D^{1/2}\right)^{-1}$$

B can be easily derived from $B_2$ and D as:

$$B = \left(1 - 4 \cdot \frac{P_1 - B_2 \cdot P_2}{\ln(D)}\right)^{-1}$$

with $$P_1 = \left(1 - \frac{2}{1+D} D^{1/4}\right), P_2 = \left(1 - \frac{2}{1+D} D^{1/2}\right); \text{ then}$$

$$R = \frac{V_2}{I_H \cdot B^2 \cdot \left(1 - \frac{2}{1+D} D^{1/2}\right)} = \frac{V_2}{I_H \cdot B^2 \cdot P_2}.$$

The solution conductivity G can be derived from the expression G=C/R, wherein C is the electrode constant.

Another exemplary solution includes the averaging of the voltages for three different periods of time ($\Delta t_1$, $\Delta t_2$, $\Delta t_3$), e.g., $\Delta t_1 = (\frac{1}{8}) \rightarrow (\frac{3}{8})T_H$, $\Delta t_2 = (\frac{3}{8}) \rightarrow (\frac{5}{8})T_H$ and $\Delta t_3 = (\frac{5}{8}) \rightarrow (\frac{7}{8})T_H$, for obtaining $V_{a1}$, $V_{a2}$ and $V_{a3}$ in order to reduce the influences of the random interferences. When $V_{a1}$, $V_{a2}$ and $V_{a3}$ are used to solve the equations, the function $V_a$ is used as described above.

$$V_a = RI_H \left\{ B^2 \left[\left(1 - \frac{2}{(1+D)} \frac{T}{T_2 - T_1}\left(D^{\frac{T_1}{T_H}} - D^{\frac{T_2}{T_H}}\right)\right] + B(1-B)\ln(D)\left[\frac{1}{2} - \frac{1}{2}\frac{(T_1 + T_2)}{T_H}\right]\right] \right\}$$

Then, the three simultaneous equations can be written as above and again D is derived from $$B_{a1} = \frac{V_{a1} + V_{a3}}{V_{a2}},$$

$B_{a2}$ is obtained from $$B_{a2} = \frac{V_{a1}}{V_{a2}},$$

and finally, R is derived from $V_{a2}$. The solution conductivity G can be derived from the expression G=C/R.

To reduce the effects of the random interferences, $V_1$, $V_2$ and $V_3$, or $V_{a1}$, $V_{a2}$ and $V_{a3}$ can be calculated by averaging the voltages of the same phase points of a plurality of voltage functions. After reversing the sign, the voltages of the negative half cycles can also be used in the calculation. $V_1$, $V_2$ and $V_3$, or $V_{a1}$, $V_{a2}$ and $V_{a3}$ are used to set up the simultaneous equations in order to obtain the three unknown values R, B and D, wherein R is the resistance between the electrodes to be measured.

In general, it is to be noted that the so-called dual-frequency method or the so-called one-frequency-triple-voltage method described above are related to a certain measurement. That is, for a certain measurement the excitation is done with a pair of frequencies or with a single frequency. It is apparent to one skilled in the art that the appropriate exciting frequency may be different when solutions within different conductivity ranges are measured. For example, the lower the conductivity of the solution a lower frequency, together with a smaller current, is used for excitation. In addition, as the conductivity of the solution is generally related to the temperature of the solution, a temperature sensor can be included in the solution conductivity sensor or electrode. Therefore, the cable connecting the sensor with the processing unit may include wires for connecting the temperature sensor. A circuit for measuring the temperature may also be provided in the processing unit. All mentioned principles are also suitable for the method of the present disclosure.

The terms, symbols, expressions and examples used in the description above are not by any means to limit the application of the disclosure, and merely for the convenience of illustration thereof.

In an exemplary embodiment of the disclosure, the frequencies $f_g$ and $f_r$ and the alternating current i are chosen for a middle range of commonly measured solutions. For example, they are chosen to be: $f_g$=1 kHz, $f_r$=2 kHz and i=0.1 mA.

The embodiments described above only represent exemplary embodiments of the present disclosure. Various equivalent substitutions and modifications can be made by one skilled in the art based on the foregoing description.

Nevertheless, all these substitutions and modifications based on the embodiments of the present disclosure fall within the spirit of the present disclosure and the scope as defined in the appended claims.

It will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

REFERENCES 1 solution
2, 102, 202 measuring cell
3, 103 connecting cable
4, 104 processing unit
5 current source
6 synchronous rectifier
7, 407 operation unit
8, 408 frequency controlling unit
106 amplifier
G conductivity of the solution
i alternating current
I current source
$f_H$, $f_L$ frequency
V voltage of the measuring cell
$V_r$ voltage after synchronous rectification
$I_H$, $I_L$ amplitude
$V_H$, $V_L$ average voltage
$R_H$, $R_L$ impedance
R resistance
n ratio of frequencies
C electrode constant
w relative difference
$w_{ref}$ reference value
Cp, Cs capacitor

What is claimed is:

1. A method for measuring an electrical resistance (R) and/or electrical conductivity (G) of a solution with a measurement device having at least one measuring cell, which is in contact with the solution and which is connected via a connecting cable to a processing unit, the method comprising:
applying a first alternating current (i) of a substantially rectangular shape and of a first frequency to the measuring cell by a current source;
measuring, by the processing unit, a first voltage ($V_1$) of the measuring cell in response to the first applied alternating current;
applying a second alternating current (i) of a substantially rectangular shape and of a second frequency different from the first frequency to the measuring cell by the current source;
measuring, by the processing unit, a second voltage ($V_2$) of the measuring cell in response to the second applied alternating current;
determining, by a calculation unit, the electrical resistance (R) and/or the electrical conductivity (G) of the solution, from the measured voltages ($V_1$, $V_2$) of the measuring cell, by solving an equation which accounts for a capacitive effect of the connecting cable,
wherein a ratio (n) between higher frequency ($f_H$) and a lower frequency ($f_L$) of the first and second frequencies is n=$f_H$/$f_L$ and is between 1.20 and 4.

2. Method according to claim 1, wherein the voltage (V) of the measuring cell is processed by a rectification process which is synchronised to the alternating current (i), and by an averaging process to provide an averaged voltage ($V_H$, $V_L$).

3. Method according to claim 2, wherein an impedance ($R_H$, $R_L$) of the solution is calculated by dividing the averaged voltage ($V_H$, $V_L$) by an amplitude ($I_H$, $I_L$) of the alternating current.

4. Method according to claim 1, wherein the resistance (R) of the solution is calculated from a first impedance ($R_H$) of the first measurement and a second impedance ($R_L$) of the second measurement.

5. Method according to claim 4, wherein the resistance (R) of the solution is calculated according to an expression:

$$R = P_{nw} R_L + (1 - P_{nw}) R_H,$$

wherein $P_{nw}$ is a function of the ratio (n) and of a relative difference (w), which is defined as w=($R_L$−$R_H$)$R_H^{-1}$.

6. Method according to claim 5, wherein a reference value ($w_{ref}$) is defined, and when the relative difference (w) is close to or smaller than the reference value ($w_{ref}$), the function $P_{nw}$ is given by: $P_{nw}$=n/(n−1).

7. Method according to claim 1, wherein a capacitive effect of the connecting cable and/or a polarization effect of the solution is accounted for in an equation, and wherein the resistance (R) of the solution is determined by solving that equation.

8. Method according to claim 7, wherein the processing unit controls generation of the alternating current (i) and/or synchronization of the alternating current (i) in relation to a rectification process and/or the synchronization of a rectification process in relation to the alternating current (i).

9. Method according to claim 8, comprising:
performing a first measurement with an alternating current (i) of a first frequency ($f_H$) and a second measurement with an alternating current (i) of a second frequency ($f_L$).

10. Method according to claim 9, wherein the voltage (V) of the measuring cell is processed by a rectification process which is synchronised to the alternating current (i), and by an averaging process to provide an averaged voltage ($V_H$, $V_L$).

11. Method according to claim 10, wherein the resistance (R) of the solution is calculated from a first impedance ($R_H$) of the first measurement and a second impedance ($R_L$) of the second measurement.

12. Method according to claim 11, comprising:
measuring the voltage (V) of the measuring cell using at least three different points in time ($t_1$, $t_2$, $t_3$) to determine at least three voltages values ($V_1$, $V_2$, $V_3$), wherein the resistance (R) is calculated by simultaneously solving at least three equations, which are given by a time dependent function of the voltage (V) of the measuring cell for each of the at least three voltages values ($V_1$, $V_2$, $V_3$).

13. Method according to claim 12, wherein the time dependent function of the voltage (V) of the measuring cell is given by the expression:

$$V = R \cdot I_H \left[ B^2 \left(1 - \frac{2}{1+D} D^{t/T_H}\right) + B(1-B)\ln(D)\left(\frac{1}{2} - \frac{t}{T_H}\right) \right]$$

wherein $$B = \frac{C_p}{C_s + C_p}, \quad D = e^{-\frac{T_H}{T}} \text{ and } T = \frac{C_s C_p}{C_s + C_p} R$$

with $C_p$ representing capacitance of a polarization effect which is generated in the solution by the measuring cell; $C_s$ representing a sum of a capacitance of the connecting cable and/or a capacitance of the processing unit and/or a distribution capacitance of the measuring cell; and $T_H$ representing the time period of a half cycle of the alternating current (i).

14. Method according to claim 1, wherein the measuring cell comprises:
at least two electrodes with one electrode connected to a common potential.

15. Method according to claim 14, wherein a capacitive effect of the connecting cable and/or of a polarization effect of a solution is accounted for in an equation, and wherein the resistance (R) of the solution is determined by solving that equation.

16. Method according to claim 1, wherein the processing unit controls generation of the alternating current (i) and/or synchronization of the alternating current (i) in relation to a rectification process and/or the synchronization of a rectification process in relation to the alternating current (i).

17. A method for measuring an electrical resistance (R) and/or electrical conductivity (G) of a solution with a measurement device having at least one measuring cell, which is in contact with the solution and which is connected via a connecting cable to a processing unit, the method comprising:
applying an alternating current (i) of a substantially rectangular shape to the measuring cell by a current source;
measuring, by the processing unit, a voltage (V) of the measuring cell in response to the applied alternating current; and
determining, by a calculation unit, the electrical resistance (R) and/or the electrical conductivity (G) of the solution, from the measured voltage (V) of the measuring cell, by solving an equation which accounts for a capacitive effect of the connecting cable, wherein the measuring of the voltage (V) of the measuring cell comprises using at least three different points in time ($t_1$, $t_2$, $t_3$) to determine at least three voltages values ($V_1$, $V_2$, $V_3$), and
wherein the resistance (R) is calculated by simultaneously solving at least three equations, which are given by a time dependent function of the voltage (V) of the measuring cell for each of the at least three voltages values ($V_1$, $V_2$, $V_3$).

18. Method according to claim 17, comprising:
determining the voltages values ($V_1$, $V_2$, $V_3$) by measuring the voltage (V) of the measuring cell during a time period ($\Delta t_1$, $\Delta t_2$, $\Delta t_3$) and by averaging the measurements over the corresponding time period ($\Delta t_1$, $\Delta t_2$, $\Delta t_3$).

19. Method according to claim 17, wherein the time dependent function of the voltage (V) of the measuring cell is given by the expression:

$$V = R \cdot I_H \left[ B^2 \left(1 - \frac{2}{1+D} D^{t/T_H}\right) + B(1-B)\ln(D)\left(\frac{1}{2} - \frac{t}{T_H}\right) \right]$$

wherein $$B = \frac{C_p}{C_s + C_p}, \quad D = e^{-\frac{T_H}{T}} \text{ and } T = \frac{C_s C_p}{C_s + C_p} R$$

with $C_p$ representing capacitance of a polarization effect which is generated in the solution by the measuring cell; $C_s$ representing a sum of a capacitance of the connecting cable and/or a capacitance of the processing unit and/or a distribution capacitance of the measuring cell; and $T_H$ representing the time period of a half cycle of the alternating current (i).

20. Method according to claim 19, wherein intermediate values $B_1$, $B_2$, D, $P_1$, $P_2$ and B are calculated using relationships:

$$B_1 = \frac{V_1 + V_3}{V_2}, \quad B_2 = \frac{V_1}{V_2}$$

$$D = \left(\frac{B_1 - 1 - \sqrt{2B_1 - 3}}{2 - B_1}\right)^4,$$

$$P_1 = \left(1 - \frac{2}{1+D} D^{1/4}\right),$$

$$P_2 = \left(1 - \frac{2}{1+D} D^{1/2}\right),$$

$$B = \left(1 - 4 \cdot \frac{P_1 - B_2 \cdot P_2}{\ln(D)}\right)^{-1},$$

and the resistance (R) of the solution is calculated according to the expression:

$$R = \frac{V_2}{I_H \cdot B^2 \ast P_2}.$$

21. A device for measuring an electrical resistance (R) and/or electrical conductivity (G) of a solution, comprising:
at least one measuring cell configured to contact a solution;
a current source configured to provide a first alternating current (i) of substantially rectangular shape and of a first frequency to the measuring cell, and to provide a second alternating current (i) of a substantially rectangular shape and of a second frequency different from the first frequency to the measuring cell;

a processing unit connected to the measuring cell via a connecting cable, the processing unit being configured to measure a first voltage ($V_1$) of the measuring cell in response to the first a lied current and to measure a second voltage ($V_2$) of the measuring cell in response to the first applied alternating current; and a calculation unit configured to calculate the electrical resistance (R) and/or the electrical conductivity (G) of the solution, from the measured voltages (V1, V2) of the measuring cell by solving an equation which accounts for a capacitive effect of the connecting cable, wherein a ratio (n) between a higher frequency ($f_H$) and a lower frequency ($f_L$) of the first and second frequencies is $n=f_H/f_L$ and is between 1.20 and 4.

22. Measurement device according to claim 21, wherein the current source comprises:

a constant current source (I) and an alternating device to reverse a direction of the constant current.

23. Measurement device according to claim 22, wherein the processing unit comprises:

a synchronous rectifier that is connected to the calculation unit, and the at least one measuring cell is connected, if appropriate via an amplifier, to an input of said synchronous rectifier.

24. Measurement device according to claim 23, wherein the calculation unit comprises:

a low pass filter, which filters and/or averages an input signal of the calculation unit.

25. Measurement device according to claim 24, wherein the calculation unit comprises:

an analog-digital converter to convert the voltage (V) of the measuring cell during a fraction of a time period of a half cycle of the alternating current (i).

26. Measurement device according to claim 25, wherein the calculation unit is configured to calculate the resistance (R) by simultaneously solving at least three equations, which are given by a dependent function of the voltage (V) of the measuring cell for each of at least three voltages values ($V_1$, $V_2$, $V_3$).

27. Measurement device according to claim 26, wherein in the measuring cell the electrodes are arranged in a single electrode configuration or in a 4-pole electrode configuration and/or in a 2-pole electrode configuration, which comprises a 2-wire connection or a 4 wire connection.

28. Measurement device according to claim 21, wherein the processing unit comprises:

a synchronous rectifier that is connected to the calculation unit, and the at least one measuring cell is connected, if appropriate via an amplifier, to an input of said synchronous rectifier.

29. Measurement device according to claim 21, wherein the calculation unit comprises:

a low pass filter which filters and/or averages an input signal of the calculation unit.

30. Measurement device according to claim 21, wherein the calculation unit comprises:

an analog-digital converter to convert the voltage (V) of the measuring cell during a fraction of a time period of a half cycle of the alternating current (i).

31. A device for measuring an electrical resistance (R) and/or electrical conductivity (G) of a solution, comprising:

at least one measuring cell, configured to contact a solution and connected via a connecting cable to a processing unit, which is configured for measuring a voltage (V) of the measuring cell and for determining, from the measured voltage (V) of the measuring cell, a resistance (R) and/or a conductivity (G) of the solution;

a current source configured to provide an alternating current (i) of substantially rectangular shape; and a calculation unit configured to calculate the resistance (R) and/or the conductivity (G) of the solution from the voltage (V) of the measuring cell in response to the alternating current by solving an equation which accounts for a capacitive effect of the connecting cable, wherein the calculation unit is configured to calculate the resistance (R) by simultaneously solving at least three equations, which are given by a dependent function of the voltage (V) of the measuring cell for each of at least three voltages values ($V_1$, $V_2$, $V_3$).

32. A device for measuring an electrical resistance (R) and/or electrical conductivity (G) of a solution, comprising:

at least one measuring cell, configured to contact a solution and connected via a connecting cable to a processing unit, which is configured for measuring a voltage (V) of the measuring cell and for determining, from the measured voltage (V) of the measuring cell, a resistance (R) and/or a conductivity (G) of the solution;

a current source configured to provide an alternating current (i) of substantially rectangular shape; and a calculation unit configured to calculate the resistance (R) and/or the conductivity (G) of the solution from the voltage (V) of the measuring cell in response to the alternating current by solving an equation which accounts for a capacitive effect of the connecting cable, wherein in the measuring cell the electrodes are arranged in a single electrode configuration or in a 4-pole electrode configuration and/or in a 2-pole electrode configuration, which comprises a 2-wire connection or a 4 wire connection.

* * * * *

UNITED STATES PATENT AND TRADEMARK OFFICE
CERTIFICATE OF CORRECTION

PATENT NO. : 8,521,442 B2
APPLICATION NO. : 12/333595
DATED : August 27, 2013
INVENTOR(S) : Changlin Wang et al.

It is certified that error appears in the above-identified patent and that said Letters Patent is hereby corrected as shown below:

In the Claims

Claim 21, Column 19, Line 6, change "a lied," to --applied--.

Signed and Sealed this
Twenty-second Day of October, 2013

Teresa Stanek Rea
*Deputy Director of the United States Patent and Trademark Office*